United States Patent [19]

Shin

[11] 4,391,977

[45] Jul. 5, 1983

[54] ADENINE PRODUCTION

[75] Inventor: Kju H. Shin, Baton Rouge, La.

[73] Assignee: Ethyl Corporation, Richmond, Va.

[21] Appl. No.: 331,036

[22] Filed: Dec. 16, 1981

[51] Int. Cl.$^3$ .......................................... C07D 473/34
[52] U.S. Cl. ................................................... 544/277
[58] Field of Search ......................... 544/277; 424/253

[56] References Cited

U.S. PATENT DOCUMENTS

| | | | |
|---|---|---|---|
| 3,287,452 | 11/1966 | Wakamatsu et al. | 260/252 |
| 3,398,149 | 8/1968 | Morita et al. | 260/252 |
| 3,427,315 | 2/1969 | Nomura et al. | 260/252 |
| 3,671,649 | 6/1972 | Yamada et al. | 260/252 |
| 4,059,582 | 11/1977 | Yonemitsu et al. | 260/252 |
| 4,092,314 | 5/1978 | Vander Zwan et al. | 544/277 |
| 4,216,317 | 8/1980 | Shuman et al. | 544/277 |

FOREIGN PATENT DOCUMENTS

| | | |
|---|---|---|
| 1949091 | 4/1970 | Fed. Rep. of Germany . |
| 1394322 | 2/1965 | France . |
| 42-7915 | 3/1967 | Japan . |
| 51-26897 | 3/1976 | Japan . |

Primary Examiner—Nicholas S. Rizzo
Attorney, Agent, or Firm—Donald L. Johnson; John F. Sieberth; Patricia J. Hogan

[57] ABSTRACT

Adenine is produced by reacting hydrogen cyanide with formamide in the presence of an ammonium salt and a catalytic amount of methyldisulfide at elevated temperature and pressure.

10 Claims, No Drawings

ADENINE PRODUCTION

BACKGROUND

Adenine is widely present in the tissues of animals and plants as a main constituent of nucleic acids and coenzymes. Adenine and its derivatives also are known as having pharmacological effects and are very useful in the medical and biochemical fields.

There are several known methods for producing adenine. For example, U.S. Pat. No. 3,287,452 discloses a method of producing adenine and 4,5-dicyanoimidazole which comprises reacting a source of hydrogen cyanide with ammonia in the liquid state in the absence of an amount of water greater than ten mole percent of the combined amounts of the hydrogen cyanide and said ammonia at a temperature of 60° C. to 150° C., wherein the mole ratio of ammonia to hydrogen cyanide is at least two to one.

U.S. Pat. No. 3,398,149 discloses a process for preparing adenine by heating formamide with a member selected from the group consisting of phosphorous trichloride, phosphorous oxychloride, phosphorous pentoxide, polyphosphoric acid, pyrophosphoric acid, tetrachloropyrophosphoric acid, thionyl chloride, sulfuryl chloride, chlorosulfonic acid and tosyl chloride within the range from about 70° C. to about 200° C. in a sealed vessel.

U.S. Pat. No. 3,427,315 discloses a process for preparing adenine or hypoxanthine wherein free formamidine is reacted in a non-aqueous solvent in the presence of ammonia with an α-amino-α-cyanoacetic acid derivative of the formula

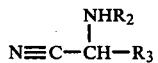

wherein $R_2$ is hydrogen, formyl, acetyl or propionyl, and $R_3$ is lower alkoxycarbonyl or carbamoyl.

U.S. Pat. No. 3,671,649 discloses a method of producing adenine and/or 4,5-dicyanoimidazole and derivatives thereof by reacting diaminomaleonitrile or diaminofumaronitrile with an amidine salt in an organic medium.

U.S. Pat. No. 4,059,582 discloses a process for preparing adenine by reacting at least one member selected from the class of diaminomaleonitrile and diaminofumaronitrile, a formic acid derivative and at least one member selected from the class of ammonia and ammonium salts in the presence or absence of a solvent.

U.S. Pat. No. 4,092,314 discloses a process for preparing 4,6-diamino-5-arylazopyrimidine from an arylazomalononitrile in the presence of ammonium chloride and formamide. The 4,6-diamino-5-arylazopyrimidine may then be hydrogenated to form 4,5,6-triaminopyrimidine which, when the hydrogenation is carried out in the presence of formic acid or its derivatives, gives adenine.

Japanese Patent Publication No. 42-7915 discloses a method of preparing adenine by reacting hydrogen cyanide with ammonia, or an alkali cyanide with ammonium salt and ammonia in the presence of formamide with heating.

Japanese Patent Publication No. 51-26897 discloses a method of preparing adenine by reacting diaminomaleonitrile or diaminofumaronitrile with formaldehyde in the presence of ammonia.

SUMMARY

In accordance with the present invention, there is provided a novel process for producing adenine in a single step and in good yields which comprises reacting hydrogen cyanide with formamide in the presence of an ammonium salt and a catalytic amount of methyldisulfide at elevated temperature and pressure.

Optionally, a catalytic amount of methyldisulfide in combination with phosphorous pentoxide may be used in the practice of the present process.

The hydrogen cyanide component of the reaction mixture may be anhydrous hydrogen cyanide in liquid or gaseous form.

The formic acid derivative component of the instant process is both a reactant and a reaction solvent. Thus, an excess of formamide is employed in the process, i.e., up to 20 moles of formamide per mole of hydrogen cyanide. Optimally, about 5 moles of formamide per mole of hydrogen cyanide are employed in the process.

The ammonium salts used in the practice of the present invention may include the ammonium salts of any inorganic or organic acid. For example, they may include ammonium acetate, sulfate, iodide, chloride, ammonium carbonate, ammonium propionate, ammonium benzoate, ammonium nitrate and the like. Ammonium acetate is the preferred ammonium salt for use in the present process. The ammonium salts are generally used in amounts of from about 0.5 mole to about 3 moles of ammonium salt per mole of hydrogen cyanide. The optimum mole ratio of ammonium salt to hydrogen cyanide is about 0.66:1.

While ammonium acetate per se can be used in the practice of the present invention, ammonium acetate can be generated in situ from gaseous ammonia and acetic acid (1:1 mole ratio) in the practice of the present process.

The reaction of the present invention is carried out at temperatures of from about 60° C. to about 180° C., preferably from about 120° C. to about 140° C. in a sealed vessel.

The reaction time may vary from approximately 1 to 20 hours. Adenine yield was found not to increase after a reaction period of 20 hours at 130° C. Typically, the reation is complete at the end of 4 hours or less.

The pressure should be high enough to maintain the reactants at least partially in the liquid state. In general, the reaction pressure is normally below approximately 100 psi.

In carrying out the reaction, methyldisulfide or a combination of methyldisulfide and phosphorous pentoxide is employed as catalysts. These are the only two catalysts found thus far to be effective in the present process. Catalysts which were found not to be effective were methylsulfide, ethylsulfide, t-butyldisulfide, benzyldisulfide, ethanethiol, methyltrisulfide, ammonium thiocyanate, thiourea, thioformamide, elemental sulfur, formic acid and polyphosphoric acid. However the combination of anhydrous phosphoric acid with methyldisulfide gave good yields of adenine but not as high as the combination of phosphorous pentoxide with methyldisulfide.

As indicated in the table below, conducting the reaction in the absence of a catalyst (methyldisulfide) produced less adenine and gave more of a black polymer by-product. In the presence of the catalyst, however, polymer production decreased and adenine yield increased. Usually, but not always, the amount of polymer increased when a catalyst was not used.

Phosphorous pentoxide itself is not as effective a catalyst as methyldisulfide. However, a mixture of methyldisulfide and a small amount of phorphorous pentoxide gave the highest yield of adenine obtained by the instant process (approximately 38%).

It is not understood at this time why only methyldisulfide or a combination of methyldisulfide and phorphorous pentoxide is an effective catalyst in the present process. A reasonable interpretation might be that the catalyst stabilizes hydrogen cyanide in such a way that the catalyst hinders the polymerization of hydrogen cyanide and drives the reaction toward adenine formation.

The amount of catalyst employed in the process is a catalytic amount. When methyldisulfide alone is used as the catalyst, a mole ratio of catalyst to hydrogen cyanide of from about 0.5 to 4 moles of catalyst per mole of hydrogen cyanide can be used. The optimum mole ratio of hydrogen cyanide to methyldisulfide at 130° C. is approximately 2.5:1. When phosphorous pentoxide is to be used in conbination with methyldisulfide, the mole ratio of methyldisulfide to phorphorous pentoxide will be from about 4 to 10 moles of methyldisulfide per mole of phosphorous pentoxide, with an optimum mole ratio of 7:1.

Hydrogen cyanide is completely consumed in the reaction. Typically, about 55% of the methyldisulfide is recovered after reaction. The fate of the rest of the catalyst is not known, however, a small percentage of the catalyst is converted to methylsulfide and methanethiol.

Adenine in the reaction mixture was quantitatively determined by HPLC with external standard. Qualitative analysis of the products was carried out with HPLC (Waters Associates, Inc., Model 244) using 82-Bondapak C18. The products were eluted with water/methanol (9/1) and detected by UV-detector. The work-up of the reaction mixture involved the following steps: centrifugation of the solids; evaporation of the volitiles and formamide solvent; solubilizing the residue with aqueous ammonium hydroxide; charcoal treatment; filtration; neutralization of the filtrate with hydrochloric acid; crystallization from the concentrated aqueous solution, and recrystallization from water.

EXAMPLE 1

This example demonstrates the preparation of adenine according to the process of the present invention.

Ammonium acetate (23.2 g, 0.301 mole) methyldisulfide (approximately 15.5 ml; 16.64 g; 0.177 mole), formamide (approximately 91 ml, 102.49 g) and phosphorous pentoxide (3.5 g; 0.0247 mole) were charged to a 300 ml Hastelloy B autoclave. The clave was cooled in an ice-salt bath. Liquid hydrogen cyanide (approximately 17 ml; 12.27 g) was weighed in a cooled syringe and injected into the clave through the injection port. The reaction was run for 4 hours at 130° C. with stirring. The pressure in the clave was about 50 psi at 130° C. After the reaction, the clave was cooled to 40° C. and the gas vented through a caustic scrubber. The mixture was discharged and the clave was rinsed with formamide. The combined mixture was centrifuged and the black solid was rinsed again with formamide and aqueous acetic acid, followed by centrifugation. The combined formamide solution (502.94 g) aqueous solution (192.73 g) were submitted for analysis.

HPLC analysis showed that adenine yield was approximately 38.0%. The mixture also contained 1.3% diaminomaleonitrile and 0.5% 4,5-dicyanoimidazole. The dried black solid (overnight at 120° C.) weighed 1.82 g (14.8% based on hydrogen cyanide). Hydrogen cyanide was completely converted.

In a similar manner, several other experiments were carried out varying the kinds and amounts of reactants and reaction conditions with the results being given in the following table.

TABLE I

Adenine Synthesis

| Exp. No. | HCN (mole) | NH$_4$OAc (mole) | (CH$_3$)$_2$S$_2$ or other sulfides | HCONH$_2$ (mole) | Time (hr) | Temp. (°C.) | NH$_3$ (mole) | Adenine % | DAMN % | DCI % | Polymer |
|---|---|---|---|---|---|---|---|---|---|---|---|
| 2 | 0.429 | 0.301 | Et—S—Et 0.178 | 2.25 | 20 | 130 | | 17.9 | 5.5 | 0.6 | 29.0 |
| 3 | 0.420 | 23.2 | 0.430 | 2.26 | 20 | 130 | | 28.6 | 2.1 | 0.7 | 9.7 |
| 4 | ~0.370 | 0.301 | 0.257 | none | 10 | 130 | | 18.3 | 13.6 | 3.0 | 18.3 |
| 5 | 0.430 | 0.301 | 0.169 | none | 10 | 130 | | 16.1 | 1.5 | 1.2 | 26.1 |
| 6 | 0.879 | 0.599 | none | none | 10 | 130 | | 11.0 | 2.5 | 0.2 | 39.0 |
| 7 | 0.451 | 0.301 | CH$_3$SCH$_3$ 0.298 | 2.27 | 20 | 130 | | 18.8 | 7.4 | 7.2 | 31.6 |
| 8 | 0.458 | 0.301 | CH$_3$S—CH$_3$ 0.299 | 2.27 | 20 | 130 | | ~19.9 | ~11.3 | ~1.7 | ~35.3 |
| 9 | 0.455 | 0.301 | | 2.26 | 2 | 130 | | | | | |
| | | | 0.190 | | 10 | 130 | | 36.8 | 5.3 | 0.8 | 8.1 |
| 10 | 0.460 | 0.301 | 0.171 | 2.28 | 2 | 130 | | | | | |
| | | | | | 10 | 130 | | 33.2 | 2.6 | 0.6 | 7.2 |
| 11 | 0.444 | 0.301 | none | 2.27 | 20 | 130 | | 19.1 | 4.9 | 0.4 | 39.6 |
| 12 | 0.448 | 0.301 | 0.177 | 2.27 | 20 | 130 | | 33.7 | 2.7 | 0.8 | 13.7 |
| 13 | 0.451 | 0.301 | S 0.19 | 2.25 | 10 | 130 | | 8.0 | 8.6 | 0.9 | 10.6 |
| 14 | | 0.301 | | 2.27 | 2 | 145 | | | | | |
| | 0.451 | | 0.178 | | 10 | 130 | | 31.0 | 3.1 | 1.0 | 8.0 |
| 15 | 0.418 | 0.301 | 0.085 | 2.276 | 20 | 130 | | 25.5 | 2.6 | 1.1 | |
| 16 | 0.428 | 0.301 | C$_2$H$_5$SH 0.172 | 2.255 | 20 | 130 | | 11.5 | 5.9 | 3.5 | 9.4 |
| 17 | | 0.301 | | 2.257 | 4 | 130 | | | | | |
| | 0.439 | | 0.175 | | 10 | 130 | | 33.2 | 3.7 | 1.2 | |
| 18 | 0.425 | 0.301 | CH$_3$S$_3$CH$_3$ 0.091 | 2.258 | | | | 19.0 | 3.2 | 1.1 | 7.4 |
| 19 | | 0.301 | | 2.270 | 1 | 130 | | | | | |

TABLE I-continued

Adenine Synthesis

| Exp. No. | HCN (mole) | NH4OAc (mole) | (CH3)2S2 or other sulfides | HCONH2 (mole) | Time (hr) | Temp. (°C.) | NH3 (mole) | Yield Adenine % | DAMN % | DCI % | Polymer |
|---|---|---|---|---|---|---|---|---|---|---|---|
|  |  | 0.433 |  | 0.176 | 10 | 130 |  | 32.1 | 2.0 | 1.1 | 7.3 |
| 20 | 0.416 | 0.301 | φCH2SSCH2φ 0.085 | 2.265 |  |  |  | 15.2 | 2.1 | 0.7 |  |
| 21 | 0.438 | 0.301 | 0.188 | 2.272 | 4 | 130 |  | 13.1 | 0.6 | 0.5 | 46.8 |
| 22 | 0.443 | 0.301 | 0.192 | 2.272 |  |  |  | 34.3 | 1.7 | 0.3 |  |
| 23 | 0.436 | 0.301 | 0.187 | 2.252 | 4 | 130 |  | 32.3 | 0.08 | 0.6 |  |
| 24 | 0.436 | 0.443 | 0.177 | 2.259 | 4 | 130 |  | 29.8 | 2.1 | 1.2 | 10.9 |
| 25 | 0.436 | 0.301 | HCSNH2 0.082 | 2.252 | 4 | 130 |  | 5.9 | 4.8 | 2.1 | 14.2 |
| 26 | 0.301 |  | NH4 SCN 0.187 | 2.261 | 3 | 130 |  | 16.7 | 5.0 | 0.4 | 27.8 |
| 27 | 0.482 | 0.301 | 0.168 | 2.246 | 0.5 3 | 130 130 | NH3 0.294 | 26.2 | 2.1 | 0.4 | 16.7 |
| 28 | 0.427 | 0.301 | thiourea 0.187 | 2.246 | 4 | 130 |  | 13.9 | 4.6 | 0.7 | 35.8 |
| 29 | 0.419 | 0.150 | 0.174 | 2.267 | 1.5 3 | 60 130 |  | 25.5 | 2.1 | 0 | 28.9 |
| 30 | 0.439 | 0.301 | 0.171 | 2.266 | 1.5 3 | 60 130 |  | 29.4 | 0.81 | 0.3 | 21.7 |
| 31 | 0.506 | 0.101 | 0.181 | 2.252 | 4 | 130 | HCOOH 0.019 | 29.8 | 0.8 | 0.3 | 11.8 |
| 32 | 0.449 | 0.301 | 0.174 | 2.251 | 4 | 130 | H3PO4 0.031 | 34.7 | 1.2 | 0.2 | 12.1 |
| 33 | 0.453 | 0.301 | — | 2.280 | 4 | 130 | H3PO4 0.031 | 19.1 | 1.0 | 1.1 | 46.8 |
| 34 | 0.454 | 0.301 | 0.177 | 2.276 | 4 | 130 | P2O5 0.025 | 38.0 | 1.3 | 0.5 | 14.8 |
| 35 | 0.441 | 0.301 | — | 2.270 | 4 | 130 | P2O5 0.025 | 18.1 | 7.1 | 0.9 | 61.6 |
| 36 | 0.444 | 0.301 | 0.176 | 0.714 | 4 | 130 | P2O5 0.025 | 27.2 | 2.1 | 0.6 | 25.0 |
| 37 | 0.445 | 0.301 | 0.173 | 2.245 | 4 | 130 | Poly H3PO4 4.99g | 31.7 | 3.2 | 0.8 | 13.6 |
| 38 | 0.435 | 0.301 | 0.173 | 1.042 | 4 | 130 | P2O5 0.025 | 30.1 | 2.6 | 0.9 | 18.1 |
| 39 | 0.446 | 0.301 | 0.176 | 2.249 | 4 | 130 | P2O5 0.074 | 33.6 | 8.4 | 2.2 | 24.5 |
| 40 | 0.439 | 0.301 | 0.169 | 2.264 | 4 | 130 | 0.049 | 32.6 | 5.2 | 1.9 | 19.0 |
| 41 | 0.449 | 0.301 | 0.171 | 1.492 | 4 | 130 | P2O5 0.025 | 28.2 | 4.5 | 0.6 | 25.1 |

Reference to the table (Exp. No. 11) shows that conducting the reaction in the absence of a catalyst (methyldisulfide) gave adenine in a yield of 19% and a large amount (40%) of the black polymer was the main product. In the presence of the catalyst, the polymer yield increased to 14% and the adenine yield increased to 34% (Exp. No. 12). Usually, but not always, the amount of the polymer increased when a catalyst was not effective.

Phosphorous pentoxide by itself was not as effective as a catalyst as methyldisulfide as demonstrated by Exp. No. 35 in the table in which an adenine yield of only 18.1% was obtained along with a 61.6% yield of black polymer. This was also the case when phosphoric acid was used as a catalyst (Exp. No. 33). However, when methyldisulfide was present, the yield of adenine increased to 38% in the case of phosphorous pentoxide (Exp. No. 34) and 34.7% in the case of phosphoric acid (Exp. No. 32).

Reference to Exp. No. 6 shows that the reaction proceeds without formamide and methyldisulfide, however a yield of only 11% of adenine was obtained.

In the presence of the catalyst, and absence of formamide, the adenine yield improved to 16-18%. (Exp. Nos. 4 and 5). The yield increased to approximately 34% when both the catalyst and formamide were present (Exp. No. 12).

It appears that the optimum mole ratio of formamide to hydrogen cyanide is about 5:1 (Exp. No. 34). Decreasing the amounts of formamide to approximately one-half and one-third of that amount resulted in a decreased yield of adenine to approximately 30% and 27%, respectively at the conditions given (Exp. Nos. 38 and 36).

Reference to Exp. No. 2 shows that ethylsulfide is not an effective catalyst in the present process, nor is methylsulfide as indicated in Exp. Nos. 7 and 9. Exp. Nos. 16 and 18 indicate that ethylmercaptan also is ineffective as is benzyldisulfide (Exp. No. 20). Thioformamide (Exp. No. 25), ammonium thiocyanate (Exp. No. 26), thiourea (Exp. No. 28) and elemented sulfur (Exp. No. 13) also were not effective in catalyzing the instant reaction.

Having disclosed the process of the present invention, one skilled in the art can readily envision variations, modifications and changes within the scope and spirit of this invention. Therefore, it is desired that the present invention be limited only by the lawful scope of the following claims.

What is claimed is:

1. A process for producing adenine which comprises reacting hydrogen cyanide with formamide in the presence of an ammonium salt and a catalytic amount of methyldisulfide at elevated temperature and pressure.

2. A process according to claim 1, wherein said reaction is carried out at a temperature in the range of from about 60° C. to about 180° and at a pressure of 100 psi or less.

3. A process according to claim 1, wherein the amount of formamide present is from about 2 to 20 moles of formamide per mole of hydrogen cyanide.

4. A process according to claim 1, wherein said ammonium salt is selected from ammonium acetate, ammonium sulfate, ammonium iodide, ammonium chloride, ammonium carbonate, ammonium propionate, ammonium benzoate and ammonium nitrate.

5. A process according to claim 1, wherein the amount of ammonium salt present is from about 0.5 to about 3 moles of ammonium salt per mole of hydrogen cyanide.

6. A process according to claim 1, wherein said ammonium salt is generated in situ from gaseous ammonia and the corresponding inorganic or organic acid.

7. A process according to claim 1, wherein said methyldisulfide is present in an amount of from about 0.5 to about 4 moles of methyldisulfide per mole of hydrogen cyanide.

8. A process according to claim 1, wherein phosphorous pentoxide is additionally present in the reaction.

9. A process according to claim 8, wherein the amount of phosphorous pentoxide present is from about 4 to 10 moles of methyldisulfide per mole of phosphorous pentoxide.

10. The process of claim 1 wherein one molar proportion of hydrogen cyanide is reacted with about 2-20 molar proportions of formamide in the presence of about 0.5-3 molar proportions of an ammonium salt and about 0.5-4 molar proportions of methyldisulfide at a temperature in the range of about 60°-180° C. and a pressure sufficient to maintain the reactants at least partially in the liquid state but not greater than about 100 psi.

* * * * *

UNITED STATES PATENT AND TRADEMARK OFFICE
CERTIFICATE OF CORRECTION

PATENT NO. : 4,391,977
DATED : July 5, 1983
INVENTOR(S) : Kju Hi Shin

It is certified that error appears in the above—identified patent and that said Letters Patent is hereby corrected as shown below:

Column 3, line 38, "82-" should read -- µ- --.

Column 5, line 47, "increased" (first instance) should read -- decreased --.

Signed and Sealed this

Twenty-ninth Day of November 1983

[SEAL]

Attest:

GERALD J. MOSSINGHOFF

Attesting Officer

Commissioner of Patents and Trademarks